United States Patent [19]

Schaefer et al.

[11] Patent Number: 5,750,590
[45] Date of Patent: May 12, 1998

[54] POLYMERIZABLE MATERIAL

[75] Inventors: Roland Schaefer, Friedrichsdorf; Detlef Heindl, Weinbach; Dieter Schödel, Wiesbaden; Oskar Nuyken, München; Ralf Böhner, Martinsried; Christoph Erdmann, Dachau, all of Germany

[73] Assignee: Heraeus Kulzer GmbH, Hanau, Germany

[21] Appl. No.: 675,612

[22] Filed: Jul. 3, 1996

Related U.S. Application Data

[63] Continuation-in-part of Ser. No. 604,906, Feb. 22, 1996, abandoned.

[30] Foreign Application Priority Data

Feb. 22, 1995 [DE] Germany ............... 195 06 222.1

[51] Int. Cl.$^6$ ........................... C08F 2/46; C08L 33/10
[52] U.S. Cl. ............... 523/115; 523/116; 523/461; 523/467; 522/31; 528/417; 524/612
[58] Field of Search ............... 523/115, 116, 523/461, 467; 522/31; 528/417; 524/612

[56] References Cited

U.S. PATENT DOCUMENTS

| | | | |
|---|---|---|---|
| 3,066,112 | 11/1962 | Bowen | 433/228.1 |
| 3,539,533 | 11/1970 | Lee, II et al. | 523/115 |
| 4,029,632 | 6/1977 | Gross et al. | 106/35 |
| 4,192,924 | 3/1980 | Crivello | 528/409 |
| 4,216,288 | 8/1980 | Crivello | 528/90 |
| 4,267,097 | 5/1981 | Michl et al. | 524/786 |
| 4,400,541 | 8/1983 | Iyer | 568/56 |
| 4,795,823 | 1/1989 | Schmitt et al. | 523/120 |
| 5,028,638 | 7/1991 | Heid et al. | 522/14 |
| 5,434,196 | 7/1995 | Ohkawa et al. | 522/170 |
| 5,521,227 | 5/1996 | Palazzotto et al. | 522/18 |

FOREIGN PATENT DOCUMENTS

| | | |
|---|---|---|
| 0 235 826 | 9/1987 | European Pat. Off. . |
| 0 382 033 | 8/1990 | European Pat. Off. . |
| 24 03 211 C3 | 7/1975 | Germany . |
| 24 05 578 C3 | 8/1975 | Germany . |
| 28 30 927 A1 | 1/1980 | Germany . |
| 30 20 092 A1 | 12/1981 | Germany . |
| 38 19 777 A1 | 12/1989 | Germany . |
| 40 01 977 C2 | 8/1991 | Germany . |
| 40 01 978 C2 | 8/1991 | Germany . |
| 42 29 947 A1 | 3/1994 | Germany . |

OTHER PUBLICATIONS

J. Am. Chem. Soc., vol. 79 (1957) 3455 and 3456.
J. Macromol. Sci. A29 (10), 915–930 (1992).
J. Macromol. Sci. A30 (2&3), 189–206 (1993).

Primary Examiner—Andrew E. C. Merriam
Attorney, Agent, or Firm—Frishauf, Holtz, Goodman, Langer & Chick, P.C.

[57] ABSTRACT

Polymerizable materials that contain "oxetanes" (trimethylene oxides) shrink only slightly when polymerized in the presence of a cationic polymerization catalyst. The materials are particular appropriate for coatings and for medical and dental purposes.

11 Claims, No Drawings ial is represented by the "hybrids", which contain both microfine fillers and conventional fillers (macrofillers). One such material is known for example from German 24 05 578 C3. It contains 30 to 80% by weight of
5,750,590

1
POLYMERIZABLE MATERIAL

This is a Continuation-in-Part application of Ser. No. 08/604,906 filed Feb. 22, 1996, now abandoned.

BACKGROUND OF THE INVENTION

The present invention concerns a polymerizable material for medical and dental purposes, for use for example as bone cement or for dental fillings, crowns, bridges, veneers, inlays, artificial teeth, soft dental-prosthesis underlinings, and for coatings.

Polymerizable dental materials have been known for many years. The first such materials consisted of mixtures of monomeric and polymeric methyl methacrylate that cure at room temperature (cold polymerization) or at higher temperatures (hot polymerization) subsequent to the addition of a catalyst or catalyst-plus-accelerator system.

The mechanical properties of the cured products were improved by using dental materials containing such additional finely ground fillers as quartz and aluminum silicate, and their appearance by the development of new catalyst systems that do not lead to discoloring and by the use of methacrylates of higher alcohols in addition to or instead of the methyl methacrylate.

Rafael L. Bowen's introduction (U.S. Pat. 3,066,112) of long-chain monomeric dimethacrylates, products of the reaction of bisphenol A and its derivatives with glycidyl methacrylate, especially bis-GMA, instead of the methyl methacrylate employed up to that time, along with finely powdered quartz glass to augment the resin matrix, signified considerable progress in the field of dental-filling materials that cure by polymerization.

An example of another composite, a dental material containing a fine-particle inorganic filler along with organic monomers, is described in U.S. Pat. No. 3,539,533. The polymerizable binder is a mixture of bis-GMA, bis-phenol A dimethacrylate, a monomeric diluent, especially tri-ethylene glycol dimethacrylate, and optionally a small amount of methacrylic acid employed with approximately 65 to 75% by weight of the inorganic filler, which may consist for example of silicon dioxide, glass, aluminum oxide, or quartz. The particles of inorganic filler can measure approximately 2 to 85 µm. To improve the bond between the resin and filler, it can be preliminarily treated with a silane, 3-methacryloyloxypropyl trimethoxysilane.

The use of microfine (microdispersed) fillers with a mean particle size of 0.01–0.4 µm will result in aesthetic looking dental-resin products that can be polished to a high gloss and will have a translucency similar to that of natural teeth (German 2 403 211 C3).

An additional step in the development of resin-based dental materials is represented by the "hybrids", which contain both microfine fillers and conventional fillers (macrofillers). One such material is known for example from German 24 05 578 C3. It contains 30 to 80% by weight of a mixture of amorphous silicic acid (pyrogenic silicon dioxide) and finely ground glass. The silicic acid is produced by flame hydrolysis and has a maximum particle size of 0.07 µm. The glass is a borosilicate glass, a glass containing barium or lanthanum oxide, or a lithium-aluminum silicate glass and has a maximal particle size of 5 µm.

Another hybrid is the dental material described in European Patent application 382 033 A2. It contains polymerizable acrylates or methacrylates and a photopolymerization catalyst (photo-activator) along with 5 to 80% by weight of a silanized glass or silanized glass ceramic with a mean particle size between 0.1 and 10 µm and 2 to 10% by weight of a surface-treated microfine filler.

One objective in the development of new dental materials is to decrease the shrinkage that accompanies polymerization.

European Patent 235 826 B1 suggests triglycolic acid diesters with (meth)acryloyloxy groups in the alcohol moiety as monomers for low-shrinkage polymerizable dental materials. Such monomers make it possible to produce dental materials without a lot of fillers that shrink as little as materials with a lot of fillers. Polymerizable materials with 15 to 60% by weight monomers with radically polymerizable double bonds, 8 to 40% by weight inorganic fillers in the form of fibers, 15 to 60% by weight inorganic fillers not in the form of fibers, and 0 to 10% by weight of auxiliaries are known from German 38 19 777 A1. The monomers are preferably acrylates and methacrylates. These materials can be hardened by polymerization (at room temperature or higher or by light) into moldings appropriate for technical, medical, and dental purposes. Hardening is accompanied by only a little polymerization shrinkage.

Materials with little polymerization shrinkage can be prepared according to German 40 01 977 C2 and 40 01 978 C2 from monomeric acrylates and/or methacrylates or from vinyl ethers and polymers soluble therein. These materials are particularly appropriate for dental purposes and can be polymerized hot, cold, or by light.

German 42 29 947 A1 describes low-shrinkage polymerizable dental cements and bone cements with better mechanical properties than those previously employed. These cements contain, first, oligomers and/or polymers of vinyl dicarboxylic-acid anhydrides and/or their copolymers with other vinyl compounds, second, mono- and/or oligo- and/or polyhydroxyfunctional compounds that react with them accompanied by ring-opening, third, inorganic fillers that react with the carboxy groups released by the ring-opening, and, finally, hardeners.

BRIEF DESCRIPTION OF THE INVENTION

The object of the present invention is a low-shrinkage polymerizable material particularly appropriate for medical and dental purposes and for making coatings.

This object is attained in accordance with the present invention by a material containing a mixture of 50 to 100% by weight of one or more cationic polymerizable compounds of the general formulas I to IV and of a cationic polymerization initiator therefor; and of 0 to 50% by weight of one or more radically polymerizable methacrylates, and of a radical-polymerization initiator therefor, whereby the content of cationic polymerization initiator is 0.3 to 4% by weight and that of the radical-polymerization initiator is 0.1 to 5% by weight.

DETAILED DESCRIPTION OF THE INVENTION

The present invention is a low shrinkage polymerizable material for dental and medical purposes and for coatings. The material contains a mixture of 50 to 100% by weight of one or more cationic polymerizable compounds of the general formulas I to IV defined below, and of a cationic polymerization initiator therefor; and of 0 to 50% by weight of one or more radically polymerizable methacrylates, and of a radical-polymerization initiator therefor, whereby the content of cationic polymerization initiator is 0.3 to 4% by weight and that of the radical-polymerization initiator is 0.1 to 5% by weight.

Formulas I to IV

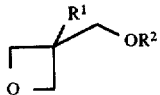   (I)

wherein $R^1$=H or a $C_{1-10}$ alkyl
and $R^2$=H, an optionally substituted $C_{1-30}$ aryl, a $C_{1-30}$ alkanoyl, or an aroyl.

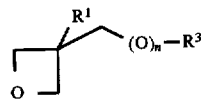   (II)

wherein $R^1$ is as defined above,
$R^3$=Si$(R^4)_3$ wherein $R^4$=an optionally substituted $C_{1-20}$ alkyl, an optionally substituted aryl, or a $C_{1-10}$ oxyalkyl; and n is 0 or 1.

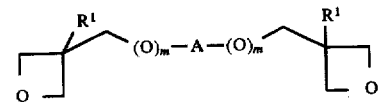   (III)

wherein $R^1$ is as defined above,
and m=0 or 1

$A = +CH_2\frac{}{n}$   $+CF_2\frac{}{n}$ n = 1–30

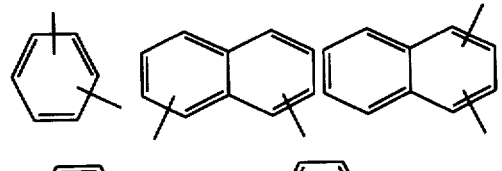

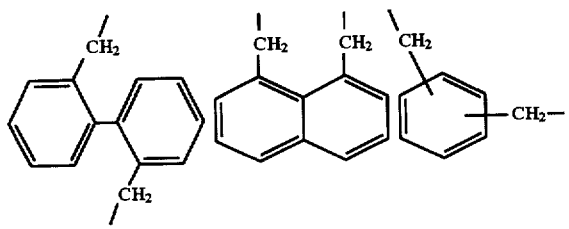

n = 1–20

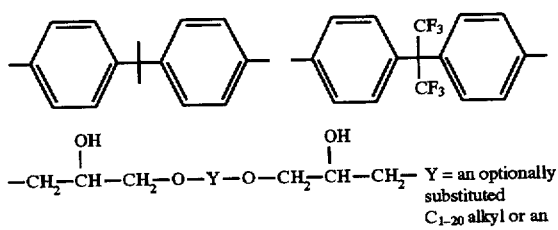

Y = an optionally substituted $C_{1-20}$ alkyl or an optionally substituted aryl

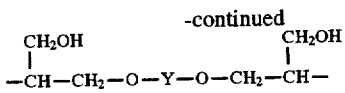

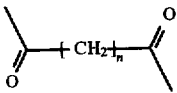

n = 1–20

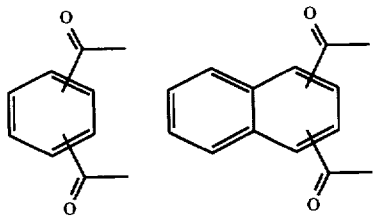

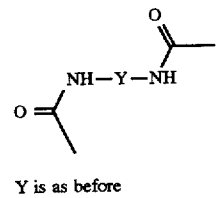

Y is as before

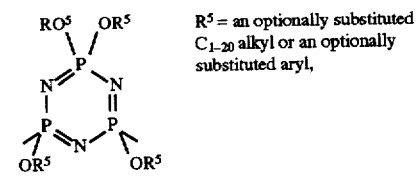

$R^5$ = an optionally substituted $C_{1-20}$ alkyl or an optionally substituted aryl,

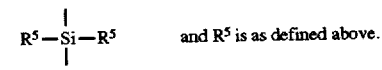 and $R^5$ is as defined above.

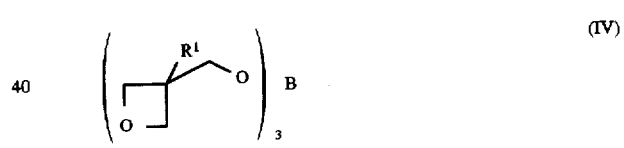   (IV)

wherein $R^1$ is as defined above and
B=an optionally substituted trivalent hydrocarbon radical, a trivalent phosphazene radical, (CONH)$_3$Z, wherein Z is an optionally substituted trivalent aliphatic or aromatic hydrocarbon radical, or

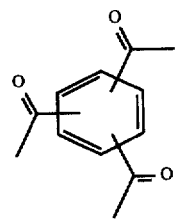

Proven to be particularly useful is a polymerizable material containing a mixture of (a) 50 to 90% by weight or one or more cationically polymerizable compounds of general formulas I through IV and of the cationic-polymerization initiator therefor; and (b) 10 to 50% by weight of one or more radically polymerizable methacrylates and of the radical-polymerization initiator therefor. The amount of cationic-polymerization initiator refers to the total amount of cationically polymerizable compounds, and the amount of cationic-polymerization initiator. Accordingly, the indicated quantity of radical-polymerization initiator refers to the total amount of radical polymerizable methacrylic acid esters and radical polymerization initiator.

The cationically polymerizable compounds of general formulas I through IV are preferably selected from the compounds

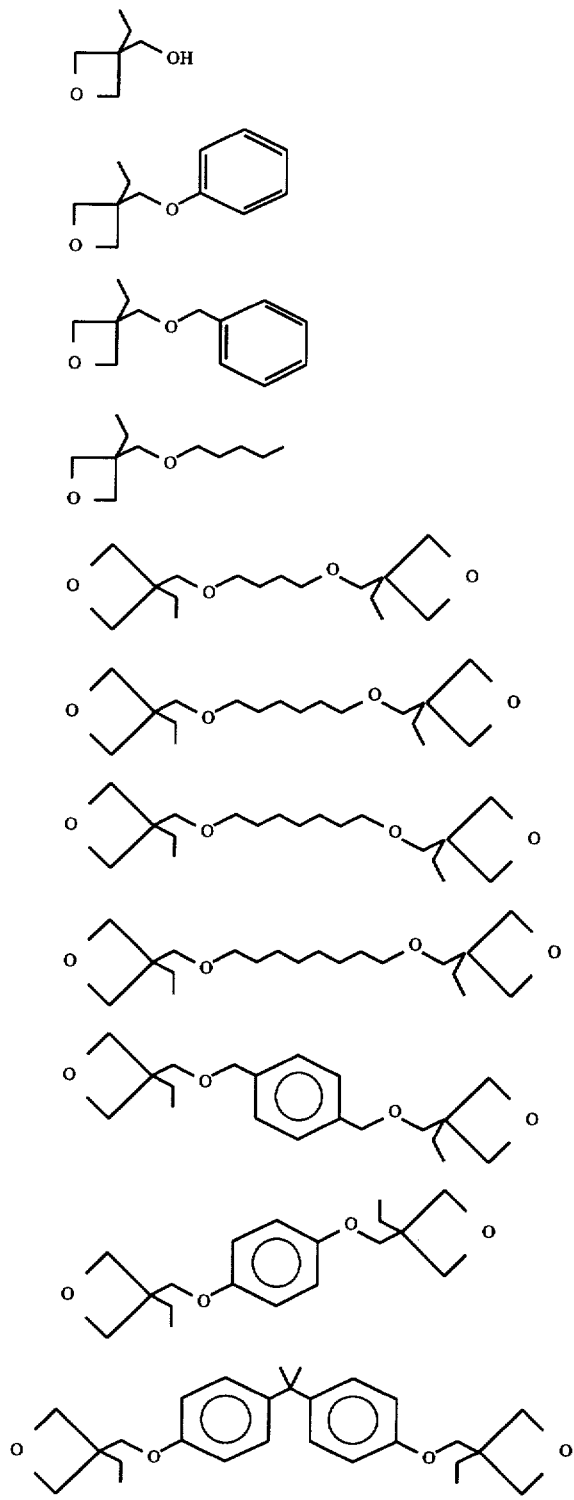

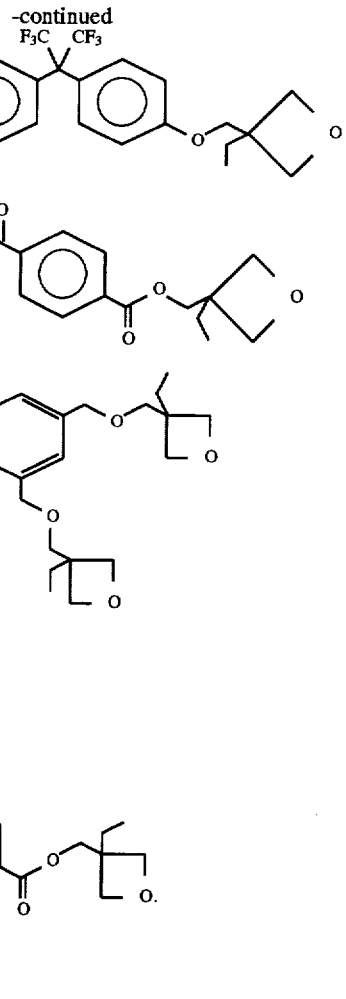

The cationically polymerizable compounds are members of the in-itself known group of oxetane (trimethylene oxide) derivatives described for example in J.Am.Chem. Soc. 79 (1957), 3455 & 3456 and in J. Macromol. Sci. A29(10) 915–930 (1992) and A30(2 & 3), 189–206 (1993). They can be prepared as shown therein.

Surprisingly, the material in accordance with the present invention shrinks very little as it polymerizes. Another advantage is the relative insensitivity of the polymerization reaction to oxygen as compared to the polymerization of methacrylates.

The polymerization of the cationically polymerizable compounds is initiated by acids, including Lewis acids. Examples are trifluoroacetic acid, sulfuric acid, and boron (III)fluoride.

Photopolymerization can occur in the presence of cationic polymerization initiators in the form of onium compounds. The salts of sulfonium, iodonium, isoquinolinium, and cyclopentadien iron(I) have been proven especially effective. [4-(Diphenylsulfonio)-phenyl]-phenylsulfide-hexafluorophosphate, bis-[4-diphenylsulfonio)-phenyl]-sulfide bis-hexafluorophosphate, (4-pentadecyloxyphenyl)-phenyliodonium hexafluorophosphate, and the associated hexafluoroarsenate, hexafluoroantimonates, and tetrafluoroborates are preferred.

The spectral sensitivity of the initiator can be increased through sensitization agents such as anthracene and perylene.

For a material containing radically polymerizable methacrylic ester, the esters of methacrylic acid with mono-, di- and polyols have proven effective. Polymerization initiators suitable for this are, for example, organic peroxides, azo compounds, redox systems, such as dibenzoylperoxide/N, N-dimethyl-p-toluidine, and, for photo-polymerization, acyl phosphine oxide (DE 28 30 927 A1, DE 30 20 092 A1), benzoin ether, a-hydroxy alkyl phenones, benzoyl-dimethyl ketal (1,2-diphenyl-2,2-dimethoxyethanone) and camphor quinone/amine systems (GB 1 408 265 B).

Likewise, fine-particle organic fillers, inorganic fillers or mixtures thereof, which are known per se, can be contained in the materials. Examples of organic fillers are homo- and copolymers of alkyl methacrylates, such as methyl methacrylate. Inorganic fillers can consist of glass, ceramic or glass-ceramic. Examples thereof are lithium, barium, strontium aluminum silicate glass, barium aluminum borosilicate glass, quartz and silica, the latter especially in the form of very fine particles (silica obtained through precipitation or flame hydrolysis). The inorganic fillers can be treated with a silane, for example, 3-methacryloyloxypropyl-trimethoxysilane.

If the materials are to be suitable for medical and dental purposes, the components forming them must be selected in such a manner that the physical, chemical, applied engineering and aesthetic requirements placed upon them are met. The formulation of such materials is known to the expert.

It has been shown that the material according to the invention is also very suitable in the manufacture of coatings for metal, ceramic, glass, wood, paper and plastic materials.

A more detailed explanation of the invention is described in the following examples wherein the preparation of several cationically polymerizable compounds, namely, of 3-ethyl-3-hydroxymethyloxetane (oxetane I), 3-ethyl-3'-hydroxymethyloxetane benzyl ether (oxetane II) and 3,3'-(p-xylylendioxymethyl)-bis-(3-ethyloxetane) (oxetane III), the determination of shrinkage during the polymerization of these three oxetanes and—for comparison—of known methacrylic acid esters (example 4) and two polymerizable materials according to the invention and their polymerization (examples 5 and 6).

The present invention will now be described with reference to examples.

EXAMPLE 1

Preparing the 3-Ethyl-3-hydroxymethyl oxetane (oxetane I)

59 g. (0.5 moles) of diethyl carbonate, 67 g (0.5 moles) of trimethyl propane, and 50 mg of potassium hydroxide dissolved in 2 ml of absolute ethyl alcohol are mixed in a protective atmosphere in a flask at room temperature. The reaction mixture is heated and refluxed 1 hour at a bath temperature of 105° to 110° C. The reflux coil is replaced with a distilling bridge or condenser and the alcohol distilled off at a bath temperature of 120° C.

3-Ethyl-3-hydroxymethyl oxetane is gradually distilled off in a vacuum while the temperature slowly increases to 180° C. The temperature must be increased slowly because of the release of carbon dioxide. The colorless liquid is fractionally distilled in a column.

Yield: 45.3 g (0.39 moles), 78% of theoretical.
Boiling point: 117° C. (at 20 mbars).
ρ: 1.0209 g cm$^{-3}$.

EXAMPLE 2

Preparing the 3-ethyl-3-hydroxymethyl oxetane benzylether (oxetane II)

42.8 g (0.25 moles) of benzyl bromide and 23.2 g (0.20 moles) of 3-Ethyl-3-hydroxymethyl oxetane are introduced into a flask. 100 g of a 50% aqueous solution of potassium hydroxide followed by 2.0 g of tetra-n-buytlammonium bromide are added at 0° C. The suspension i stirred 24 hours at room temperature. The batch is introduced into a separating funnel and shaken out once with diethyl ether. The ether phase is washed twice with water and dried on sodium sulfate. The ether is extracted and the residue fractionally distilled in a vacuum.

Yield: 24.1 g (0.117 moles), 58% of theoretical.
Boiling point: 82° C. (at 0.02 mbars).
ρ: 1.0263 g cm$^{-3}$.

EXAMPLE 3

Preparing the 3,3'-(p-xylylene-dioxymethyl)-bis-(3-ethyl oxetane) (oxetane III)

8.7 g (0.033 moles) of 1,4-dibromoxylol( 1,4-dibromomethylbenzol), and 11.6 g (0.100 moles) of 3-ethyl-3-hydroxymethyl oxetane are introduced into a flask. 17 g of a 50% aqueous solution of potassium hydroxide followed by 0.33 g of tetra-n-buytlammonium bromide are added at 0° C. The suspension is stirred 24 hours at room temperature. The batch is introduced into a separating funnel and shaken out once with diethyl ether. The ether phase is washed twice with water and dried on sodium sulfate. The ether is extracted and the residue fractionally distilled in a vacuum.

Yield: 8.4 g (0.025 moles), 76% of theoretical.
Boiling point: 173° C. (at 0.01 mbars).
Melting point: 32° C.
ρ: 1.0652 g cm$^{-3}$

EXAMPLE 4

Detecting Shrinkage During Polymerization

3-Ethyl-3-hydroxymethyl oxetane (oxetane I), 3-ethyl-3-hydroxymethyl oxetane benzylether (oxetane II), and 3,3'-(p-xylylene-dioxymethyl)-bis-(3-ethyloxetane) (oxetane III) were polymerized in a Heraeus Kulzer Unilux AC lamp system as will now be described. A ring of Teflon 1 mm thick was cemented with ordinary household adhesive between two panes of quartz glass. The monomer, which had been stored with a photo-initiator (Degacure KI 85[1]) in opaque containers, was injected inside the ring. No air bubbles were allowed inside during this procedure. The panes were then secured separated in an infrared device and laid horizontally on the system's platform. They were then irradiated with 20 units.

The density of the monomers was measured at 20° (with a digital densimeter). The results are obtained electronically from long-term frequency or oscillation measurements.

The density of the polymers was determined by the suspension method. The test was conducted four weeks after the actual polymerization in order to exclude late polymerization as much as possible. To ensure reproducible results, three samples of polymer of different size but from the same batch were employed. Their tendency to sink or float in a saline solution was observed. The step was repeated three times and the mean calculated.

Shrinkage was calculated from the formula $$\text{shrinkage} = (\text{density}_{monomer} - \text{density}_{polymer})/\text{density}_{monomer} \cdot 100\%.$$

The polymerization shrinkage S for the three oxetanes and two methacrylates are shown in the following table along with the molecular weights MW and their relation S/MW to shrinkage.

| Monomer | Shrinkage S % by vol | Molecular weight MW | S/MW |
|---|---|---|---|
| Oxetane I | 7.8 | 116 | 0.067 |
| Oxetane II | 4.9 | 216 | 0.022 |
| Oxetane III | 3.9 | 334 | 0.011 |
| Methyl methacrylate | 21.3 | 100 | 0.213 |
| Triethyleneglycol dimethacrylate | 12.0 | 286 | 0.044 |

Example 5. Photopolymerization hardening material

| | % by weight |
|---|---|
| Oxetane III | 39.0 |
| Oxetane I | 10.0 |
| bis-GMA | 48.0 |
| Degacure KI 85 (bis-(4-(diphenylsulfonio)-phenyl)-sulfide bis-hexafluorophosphate) | 2.5 |
| Lucirin LR 8728 (2,4,6-trimethylbenzoyldiphenylphosphine oxide) | 0.5 |

This material was cured in light in a Heraeus Kulzer Dentacolor XS for 90 seconds.

EXAMPLE 6

Photopolymerization Hardening Material

| | % by weight |
|---|---|
| Oxetane III | 9.75 |
| Oxetane I | 2.50 |
| bis-GMA | 12.00 |
| Degacure KI 85 (bis-4-(diphenylsulfonio)-phenyl)-sulfide bis-hexafluorophosphate) | 0.62 |
| Lucirin LR 8728 (2,4,6-trimethylbenzoyldiphenylphosphine oxide) | 0.13 |
| Lithium-aluminum silicate, mean particle size 5 μm | 75.00 |

This material was cured in light in a Heraeus Kulzer Translux for 60 seconds.

It will be appreciated that the instant specification set forth by way of illustration and not limitation, and that various modifications and changes may be made without departing from the spirit and scope of the present invention.

What is claimed is:

1. A polymerizable material consisting essentially of a mixture of (a) 50 to 90% by weight of one or more cationically polymerizable compounds and an onium compound as a cationic polymerization initiator therefor, and (b) 10 to 50% by weight of one or more free-radically polymerizable methacrylates and a camphorquinone-amine system as a free-radical polymerization initiator therefor, and wherein the content of the cationic polymerization initiator is 0.3 to 4% by weight and that of the free-radical polymerization initiator is 0.1 to 5% by weight; and, optionally, (c) a fine-particle organic filler, a fine-particle inorganic filler, or a combination thereof wherein the cationically polymerizable compounds are one or more of the compounds

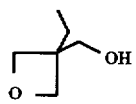

-continued

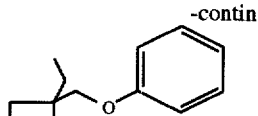

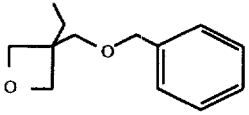

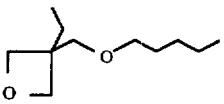

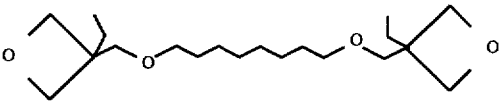

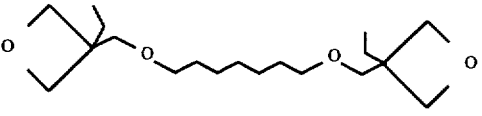

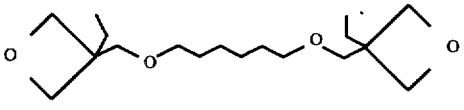

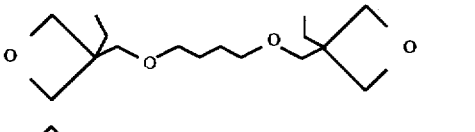

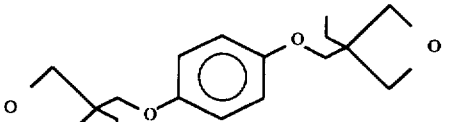

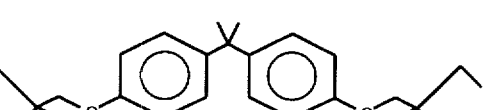

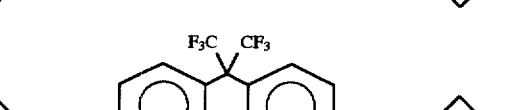

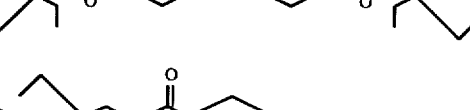

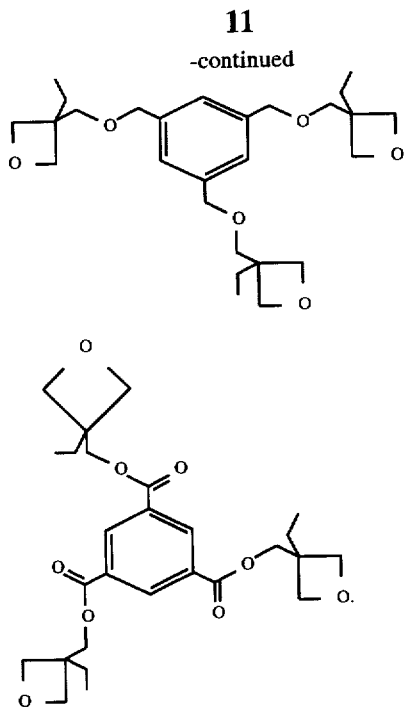

2. Polymerizable material as claimed in claim 1, wherein the content of cationic-polymerization initiator is 0.5 to 1.5% by weight and the content of the radical-polymerization initiator is 0.3 to 1% by weight.

3. Polymerizable material as claimed in claim 1, wherein the cationic photopolymerization initiator is in the form of a sulfonium salt.

4. Polymerizable material as claimed in claim 1, wherein the cationic photopolymerization initiator is in the form of an iodonium salt.

5. Polymerizable material as claimed in claim 1, wherein (a) the content of cationic-polymerization initiator is 0.5 to 1.5% by weight and the content of the radical-polymerization initiator is 0.3 to 1% by weight; (b) the cationic photopolymerization initiator is in the form of a sulfonium salt or an iodonium salt and (c) the radical-photopolymerization initiator is a camphorquinone-amine system.

6. Polymerizable material as claimed in claim 1, further containing 20 to 95% by weight of the polymerizable mixture and 5 to 80% by weight of fine-particle organic filler, fine-particle inorganic filler, or a combination thereof.

7. Polymerizable material as in claim 6, wherein the fine-particle organic filler is an alkyl-methacrylate homopolymer or copolymer.

8. Polymerizable material as claimed in claim 6, wherein the fine-particle inorganic filler is a lithium-aluminum, barium-aluminum, or strontium-aluminum silicate glass, a barium-aluminum borosilicate glass, silicon dioxide, or a mixture thereof.

9. Dental material essentially consisting of a polymerizable material as claimed in claim 1.

10. Bone cement essentially consisting of a polymerizable material as claimed in claim 1.

11. Coating materials essentially consisting of a polymerizable material as claimed in claim 1, for the manufacture of coatings for ceramic, glass, metal, wood, paper or plastic.

* * * * *